(12) United States Patent
Abdul-Hafiz et al.

(10) Patent No.: US 7,096,054 B2
(45) Date of Patent: Aug. 22, 2006

(54) LOW NOISE OPTICAL HOUSING

(75) Inventors: Yassir Abdul-Hafiz, Irvine, CA (US); John Schmidt, Lake Forest, CA (US)

(73) Assignee: Masimo Corporation, Irvine, CA (US)

( * ) Notice: Subject to any disclaimer, the term of this patent is extended or adjusted under 35 U.S.C. 154(b) by 333 days.

(21) Appl. No.: 10/632,012

(22) Filed: Jul. 31, 2003

(65) Prior Publication Data

US 2004/0039272 A1 Feb. 26, 2004

Related U.S. Application Data

(60) Provisional application No. 60/400,177, filed on Aug. 1, 2002.

(51) Int. Cl.
*A61B 5/00* (2006.01)

(52) U.S. Cl. ..................... 600/344; 600/310

(58) Field of Classification Search ........ 600/309–310, 600/323, 344; 439/43, 55
See application file for complete search history.

(56) References Cited

U.S. PATENT DOCUMENTS

| | | | |
|---|---|---|---|
| 4,685,464 A | 8/1987 | Goldberger et al. | |
| 4,700,708 A * | 10/1987 | New et al. .................. | 600/331 |
| 4,960,128 A | 10/1990 | Gordon et al. | |
| 4,964,408 A | 10/1990 | Hink et al. | |
| 4,974,591 A * | 12/1990 | Awazu et al. ............... | 600/344 |
| 5,041,187 A | 8/1991 | Hink et al. | |
| 5,069,213 A | 12/1991 | Polczynski | |
| 5,163,438 A | 11/1992 | Gordon et al. | |
| 5,337,744 A | 8/1994 | Branigan | |
| D353,195 S | 12/1994 | Savage et al. | |
| D353,196 S | 12/1994 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,562,002 A | 10/1996 | Lalin | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |

(Continued)

*Primary Examiner*—Eric F. Winakur
(74) *Attorney, Agent, or Firm*—Knobbe, Martens, Olson & Bear, LLP

(57) ABSTRACT

Aspects of the invention include an optical housing including a substrate having a reflective side and an absorbing side. The substrate has a generally planar base portion and a protruding cover portion. The cover portion defines a pocket on the absorbing side. The substrate has an open position where the base portion is distal the cover and a closed position where the base portion is proximate the cover. The substrate is configured to enclosed a detector within the pocket in the closed position. The base portion defines an aperture generally centered within the base portion and aligned with the detector in the closed position so as to pass light through to the detector.

16 Claims, 17 Drawing Sheets

U.S. PATENT DOCUMENTS

| | | |
|---|---|---|
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,236,872 B1 | 5/2001 | Diab et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,371,921 B1 | 4/2002 | Caro et al. |
| 6,377,829 B1 | 4/2002 | Al-Ali |
| 6,388,240 B1 | 5/2002 | Schulz et al. |
| 6,397,091 B1 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B1 | 12/2002 | Diab et al. |
| 6,515,273 B1 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B1 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B1 | 7/2003 | Cybulski et al. |
| 6,597,933 B1 | 7/2003 | Kiani et al. |
| 6,606,511 B1 | 8/2003 | Ali et al. |
| 6,632,181 B1 | 10/2003 | Flaherty et al. |
| 6,640,116 B1 | 10/2003 | Diab |
| 6,643,530 B1 | 11/2003 | Diab et al. |
| 6,650,917 B1 | 11/2003 | Diab et al. |
| 6,654,624 B1 | 11/2003 | Diab et al. |
| 6,658,276 B1 | 12/2003 | Kianl et al. |
| 6,661,161 B1 | 12/2003 | Lanzo et al. |
| 6,671,531 B1 | 12/2003 | Al-Ali et al. |
| 6,678,543 B1 | 1/2004 | Diab et al. |
| 6,684,090 B1 | 1/2004 | Ali et al. |
| 6,684,091 B1 | 1/2004 | Parker |
| 6,697,656 B1 | 2/2004 | Al-Ali |
| 6,697,658 B1 | 2/2004 | Al-Ali |
| RE38,476 E | 3/2004 | Diab et al. |
| 6,699,194 B1 | 3/2004 | Diab et al. |
| 6,714,804 B1 | 3/2004 | Al-Ali et al. |
| RE38,492 E | 4/2004 | Diab et al. |
| 6,721,585 B1 | 4/2004 | Parker |
| 6,725,075 B1 | 4/2004 | Al-Ali |
| 6,735,459 B1 | 5/2004 | Parker |
| 6,745,060 B1 | 6/2004 | Diab et al. |
| 6,760,607 B1 | 7/2004 | Al-All |
| 6,770,028 B1 | 8/2004 | Ali et al. |
| 6,771,994 B1 | 8/2004 | Kiani et al. |
| 6,792,300 B1 | 9/2004 | Diab et al. |
| 6,813,511 B1 | 11/2004 | Diab et al. |
| 6,816,741 B1 | 11/2004 | Diab |
| 6,822,564 B1 | 11/2004 | Al-Ali |
| 6,826,419 B1 | 11/2004 | Diab et al. |
| 6,830,711 B1 | 12/2004 | Mills et al. |
| 6,850,787 B1 | 2/2005 | Weber et al. |
| 6,850,788 B1 | 2/2005 | Al-Ali |
| 6,852,083 B1 | 2/2005 | Caro et al. |
| 6,861,639 B1 | 3/2005 | Al-Ali |
| 6,898,452 B1 | 5/2005 | Al-Ali et al. |
| 6,920,345 B1 | 7/2005 | Al-Ali et al. |
| 6,931,268 B1 | 8/2005 | Kiani-Azarbayjany et al. |
| 6,934,570 B1 | 8/2005 | Kiani et al. |
| 6,939,305 B1 | 9/2005 | Flaherty et al. |
| 6,943,348 B1 | 9/2005 | Coffin, IV |
| 6,950,687 B1 | 9/2005 | Al-Ali |
| 6,961,598 B1 | 11/2005 | Diab |
| 6,970,792 B1 | 11/2005 | Diab |
| 6,979,812 B1 | 12/2005 | Al-Ali |
| 6,985,764 B1 | 1/2006 | Mason et al. |
| 6,993,371 B1 | 1/2006 | Kiani et al. |
| 6,996,427 B1 | 2/2006 | Ali et al. |
| 6,999,904 B1 | 2/2006 | Weber et al. |

\* cited by examiner

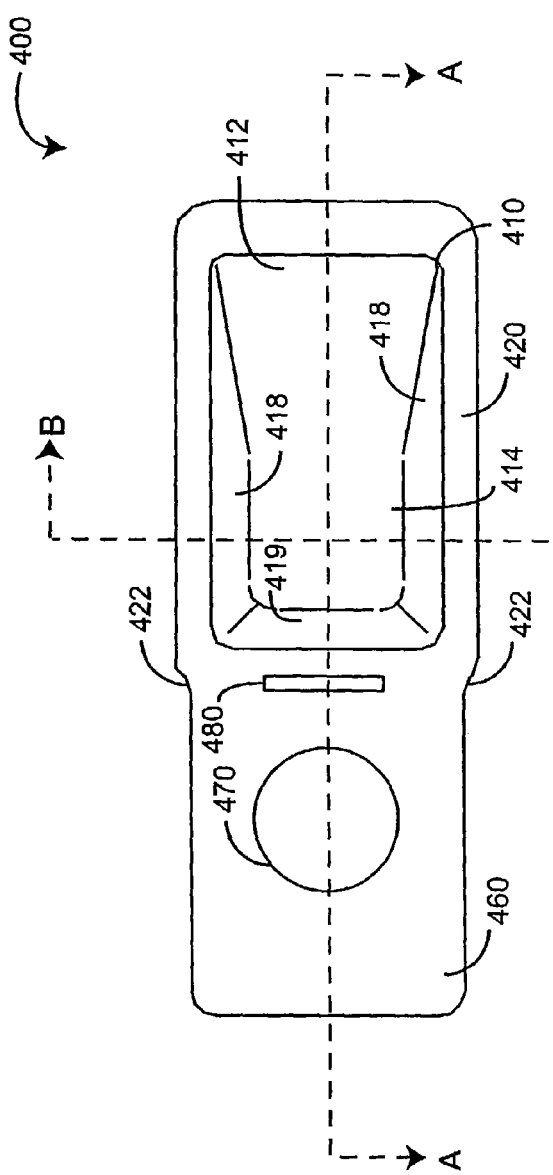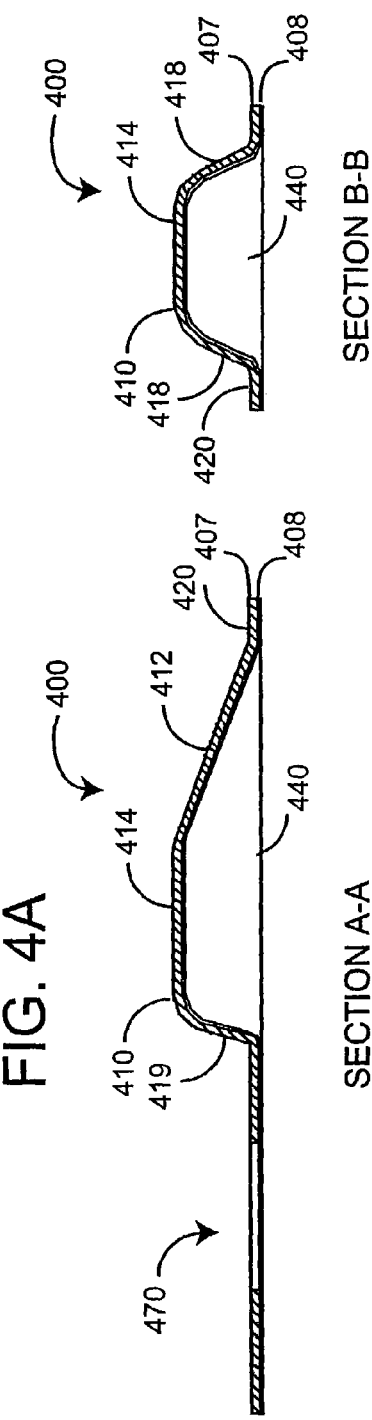

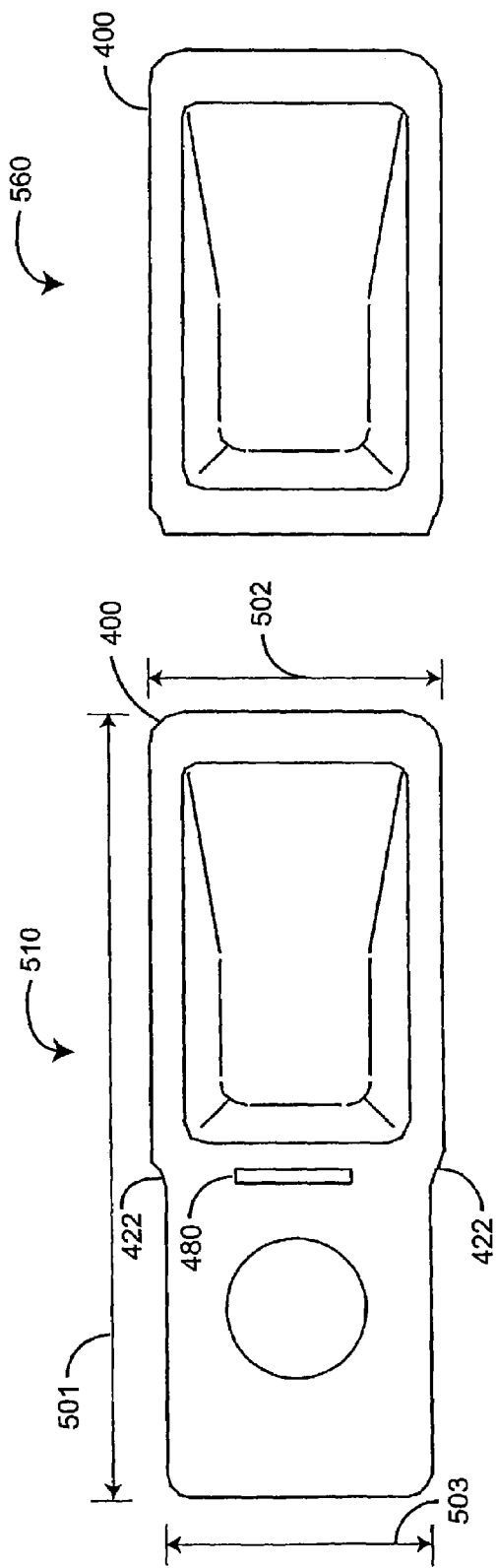
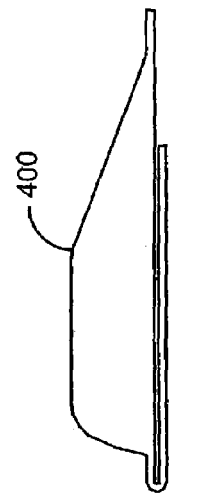
FIG. 5C
FIG. 5D
FIG. 5A
FIG. 5B
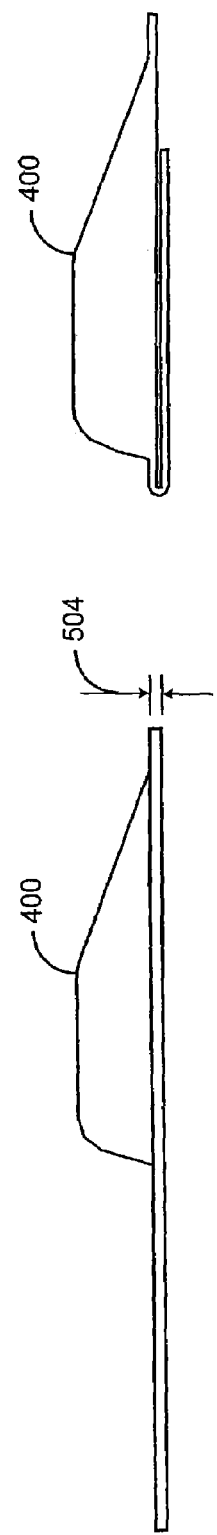

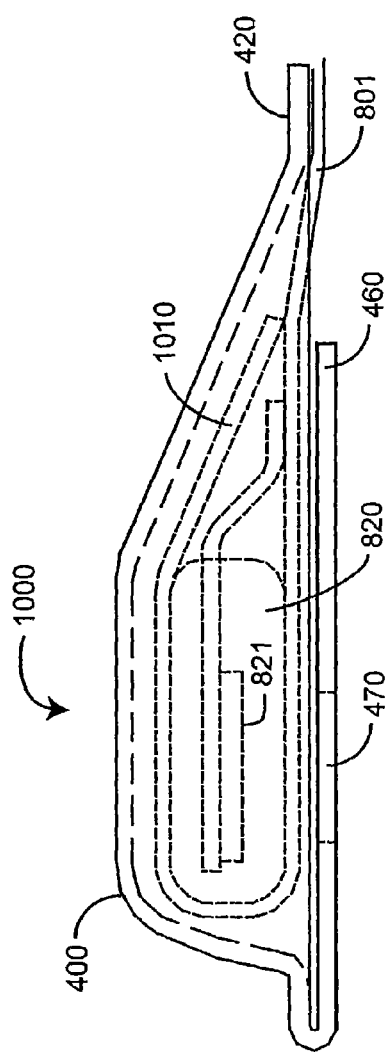
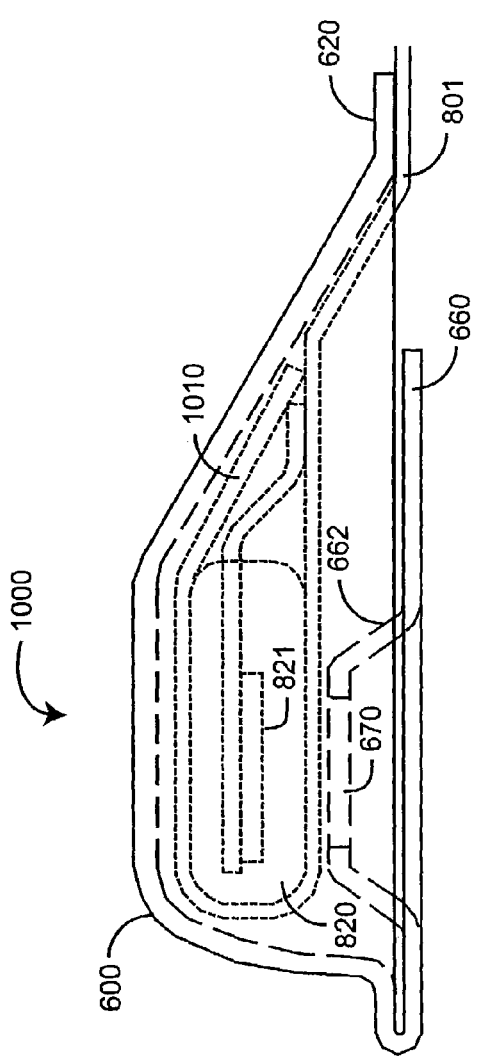

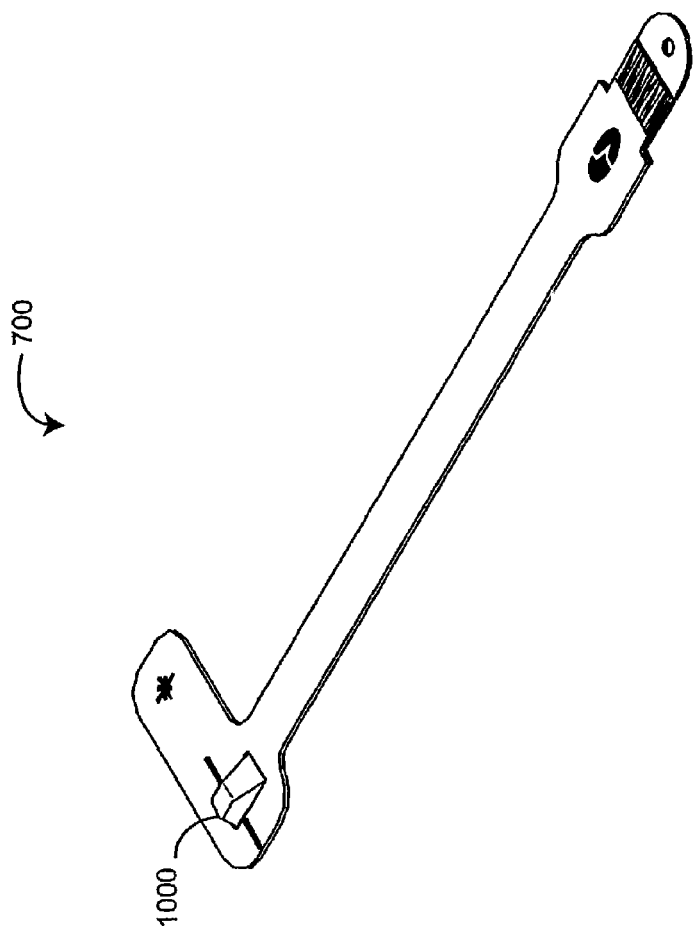
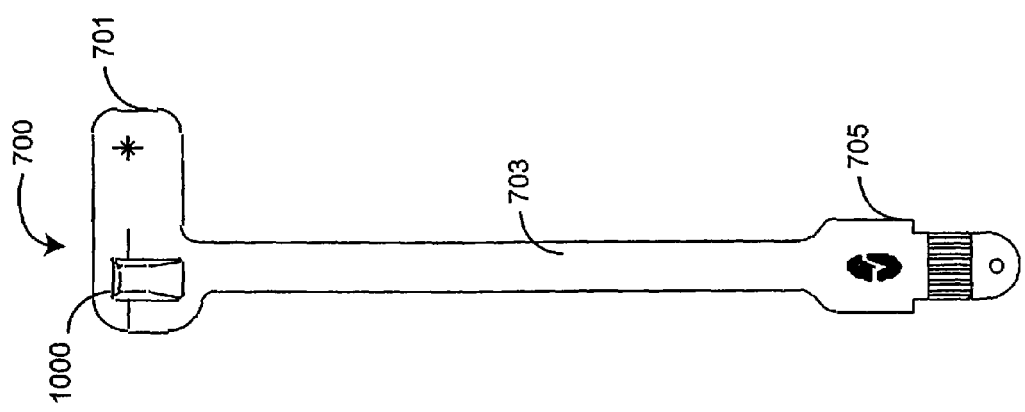
FIG. 7B
FIG. 7A

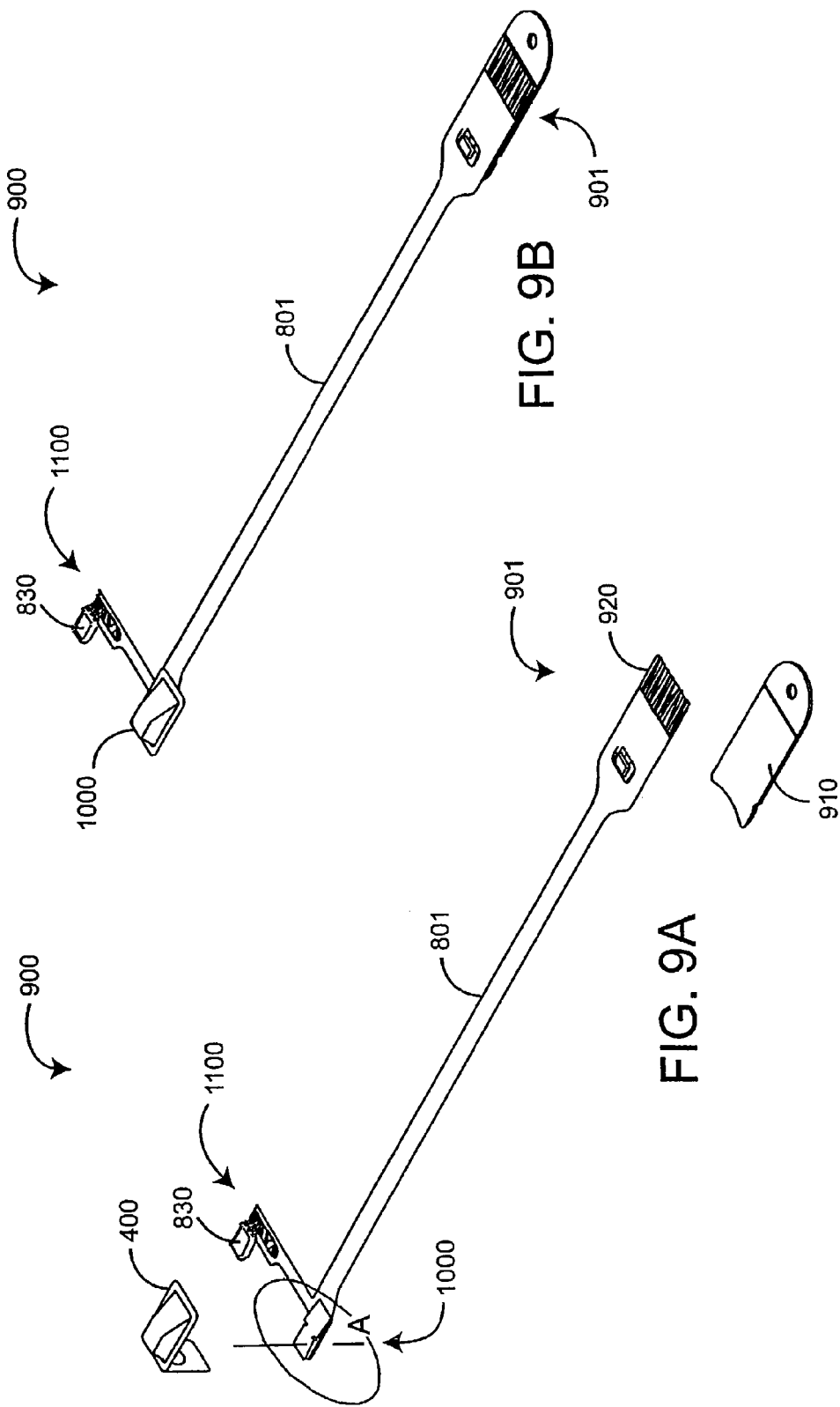

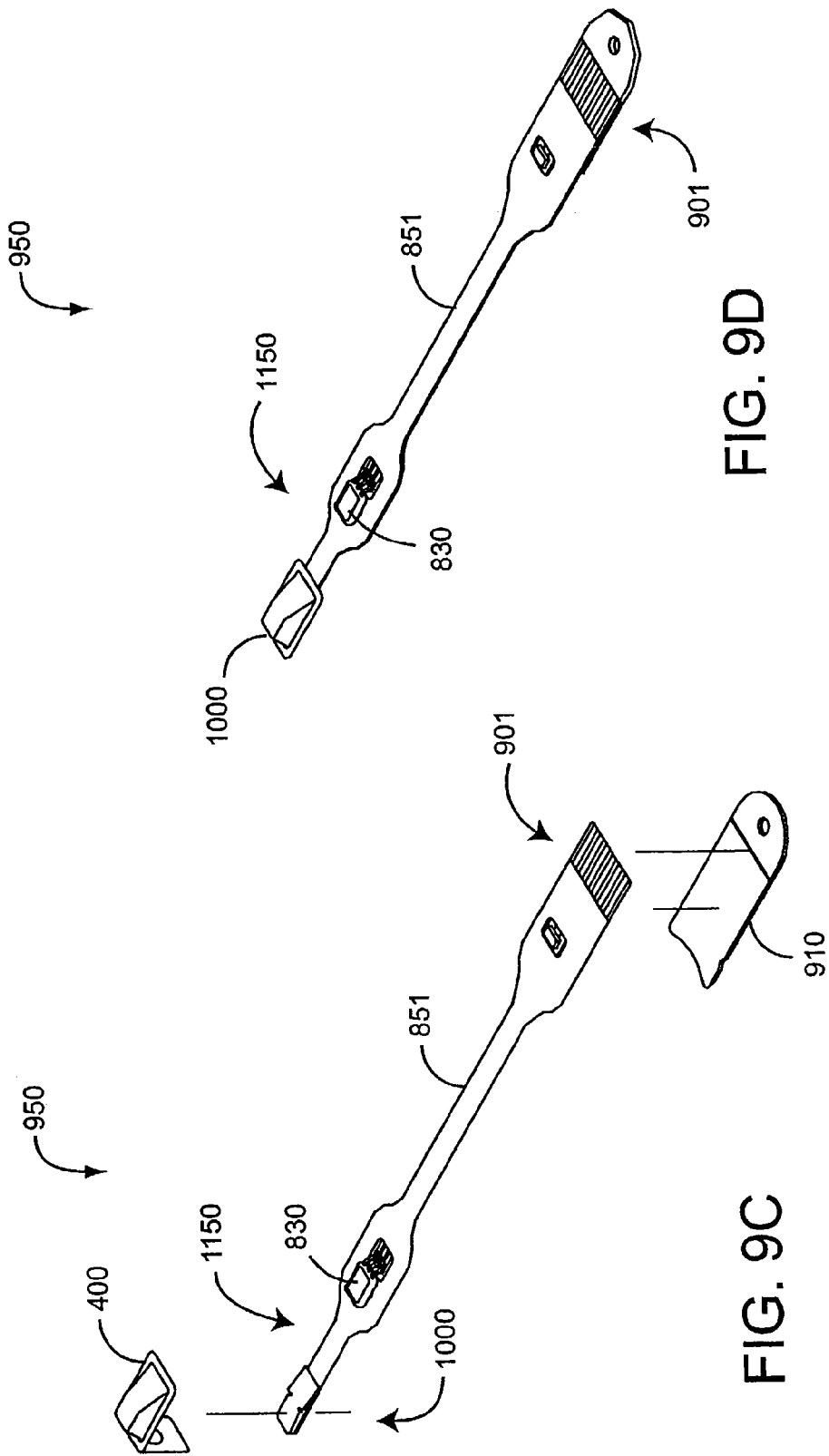

DETAIL A

DETAIL A

DETAIL A

LOW NOISE OPTICAL HOUSING

REFERENCE TO RELATED APPLICATION

This application claims the benefit of U.S. Provisional Application No. 60/400,177, Aug. 1, 2002. The present application incorporates the foregoing disclosures herein by reference.

BACKGROUND OF THE INVENTION

Pulse oximetry is a widely accepted noninvasive procedure for measuring the oxygen saturation level of arterial blood, an indicator of a person's oxygen supply. Early detection of low blood oxygen level is critical in the medical field, for example in critical care and surgical applications, because an insufficient supply of oxygen can result in brain damage and death in a matter of minutes. FIG. 1 illustrates a pulse oximetry system 100 having a sensor 110 applied to a patient, a monitor 160 and a patient cable 140 connecting the sensor 110 and the monitor 160. The sensor 110 is attached to a tissue site, such as an adult patient's finger (as shown). Other sensor types are configured to attach, say, to a neonatal patient's foot. The sensor 110 is configured with both red and infrared LEDs 112 (hidden) that, for finger attachment, project light through the fingernail and into the blood vessels and capillaries underneath. A photodiode 114 (not visible) is positioned at the finger tip opposite the fingernail so as to detect the LED emitted light as it emerges from the finger tissues.

SUMMARY OF THE INVENTION

FIG. 2 illustrates various optical noise sources for a sensor 110 (FIG. 1). Shown is the placement of the sensor LEDs 112 and detector 114 on a finger without showing the associated electrical interconnections, base stock and face stock materials. Emitted light 210 is projected from the LEDs 112 into the fingernail bed. Received light 220 propagates through the finger tissues to the detector 114, subject to absorption and scattering, to generate a desired sensor signal. Light which illuminates the detector 114 without propagating through the finger is unwanted optical "noise" that corrupts the desired sensor signal. Noise sources include ambient light 230 and piped light 240. Ambient light 230 is transmitted to the detector 114 from external light sources, i.e. light sources other than the LEDs 112. Piped light 240 is stray light from the LEDs 112 that is transmitted around a tissue site along a light conductive surface, such as a reflective inner surface of face stock material, directly to the detector 114. Light piping and light piping reduction are described in U.S. Pat. No. 5,782,757 entitled "Low Noise Optical Probe," which is assigned Masimo Corporation, Irvine, Calif. and incorporated by reference herein.

FIG. 3 illustrates a prior art low noise sensor 300. The sensor 300 has a detector 310, a spacer 330 and an optical shield 350. The detector 310 is configured to receive light 220 that has propagated through a tissue site 10, as described with respect to FIGS. 1–2, above. The spacer 330 is positioned between the tissue site 10 and the detector 310, providing an optical barrier so as to reduce the intensity of piped light 240 that reaches the detector 310. The spacer 330 defines an aperture 332 that allows a transmitted portion 360 of propagated light 220 to reach the detector 310. A blocked portion 370 of propagated light 220 is reflected back into the tissue and/or absorbed by the spacer 330, depending upon the spacer material. The optical shield 350 may be a metal foil or other opaque material that prevents ambient light 230 from reaching the detector 310. Further, the detector 310, spacer 330 and optical shield 350 may be enclosed in a housing (not shown) of opaque material that further prevents ambient light 230 from reaching the detector 310. A low noise sensor is described in U.S. Pat. No. 5,782,757, cited above.

One aspect of a low noise optical housing is a substrate having a reflective side and an absorptive side. The substrate has a generally planar base portion and a protruding cover portion. The cover portion defines a pocket on the absorptive side. The substrate has an open position with the base portion distal the cover portion and a closed position with the base portion proximate the cover portion. The substrate is configured to enclosed a detector within the pocket in the closed position. The base portion defines an aperture generally centered within the base portion and aligned with the detector in the closed position so as to pass light through to the detector.

Another aspect of a low noise optical housing is a method comprising the steps of providing a substrate having an absorptive side and a reflective side and forming a cover portion of the substrate so as to create a pocket on the absorptive side. Further steps include punching the substrate so as to separate a housing from the substrate, securing a the pocket, and enclosing the detector with the housing.

A further aspect of a low noise optical housing comprises a light reflecting cover means for shielding against ambient light and a base means for blocking piped light. The base means adjoins the cover means. The housing also comprises a light absorbing pocket means for securing a detector. The pocket means is defined by the cover means and the base means. The housing further comprises an aperture means for allowing light transmitted through a tissue site to be received by the detector. The aperture means is defined by the base means.

One aspect of a sensor circuit comprises a circuit substrate, a pair of pads disposed on an optical portion of the circuit substrate, a plurality of pinouts disposed on a connector portion of the circuit substrate, and a plurality of conductive paths providing electrical communication between the pads and the pinouts. The pads are configured to mechanically mount a corresponding pair of optical components to the circuit substrate and to electrically connect the components to the conductive paths. At least one of the pads is adapted to mount one of the components at either a first spacing or a second spacing from another one of the components. The second spacing is greater than the first spacing by a predetermined mount.

Another aspect of a sensor circuit comprisesa flexible circuit substrate, a first pad disposed on the circuit substrate and configured to mount a detector, and a second pad disposed on the circuit substrate and configured to mount an emitter. At least one of the first pad and the second pad are adapted so that a detector-emitter spacing is a first distance or a second distance depending on the placement of at least one of the detector and the emitter. The first distance and the second distance are predetermined so as to accommodate particular sensor types.

A further aspect of a sensor circuit is a method comprising the step of predetermining a plurality of optical component spacings based upon a corresponding plurality of sensor types. The sensor types are indicative of tissue site location and patient size. Further steps are configuring a pad to fixedly mount and electrically connect an optical component to a flexible circuit at a plurality of positions, where the positions correspond to the spacings, and mounting the optical component to a particular one of the positions to construct a particular one of the sensor types.

An additional aspect of a sensor circuit is a sensor comprising a circuit substrate means for mounting and electrically connecting components and a pad means disposed on the circuit substrate for fixedly mounting an emitter at either a first spacing or at a second spacing from a detector. The sensor also comprises a tape stock means for attaching the emitter and the detector to a tissue site.

For purposes of summarizing the invention, certain aspects, advantages and novel features of the invention have been described herein. Of course, it is to be understood that not necessarily all such aspects, advantages or features will be embodied in any particular embodiment of the invention.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements. In addition, the first digit of each reference number indicates the figure in which the element first appears.

FIGS. 4A–C are top, side cross-section and front cross-section views, respectively, of a low noise optical housing;

FIGS. 5A–B are top arid side views of a low noise optical housing in an open position;

FIGS. 5C–D are top and side views of a low noise optical housing in a closed position;

FIGS. 6A–B are detailed side views of alternative embodiments of a low noise optical housing enclosing a detector;

FIGS. 7A–B are top and perspective views, respectively, of an assembled pulse oximetry sensor configured for a neonate and incorporating a low noise optical housing;

FIGS. 9A–B are perspective views of a neonate sensor assembly showing installation of a low noise optical housing;

FIGS. 9C–D are perspective views of an adult sensor assembly showing installation of a low noise optical housing;

FIG. 11C shows an optical assembly without the emitter installed;

FIG. 11D shows an optical assembly with pediatric detector-emitter spacing; and

FIG. 11E shows an optical assembly with adult detector-emitter spacing; and

DETAILED DESCRIPTION OF THE PREFERRED EMBODIMENT

Figure 3:
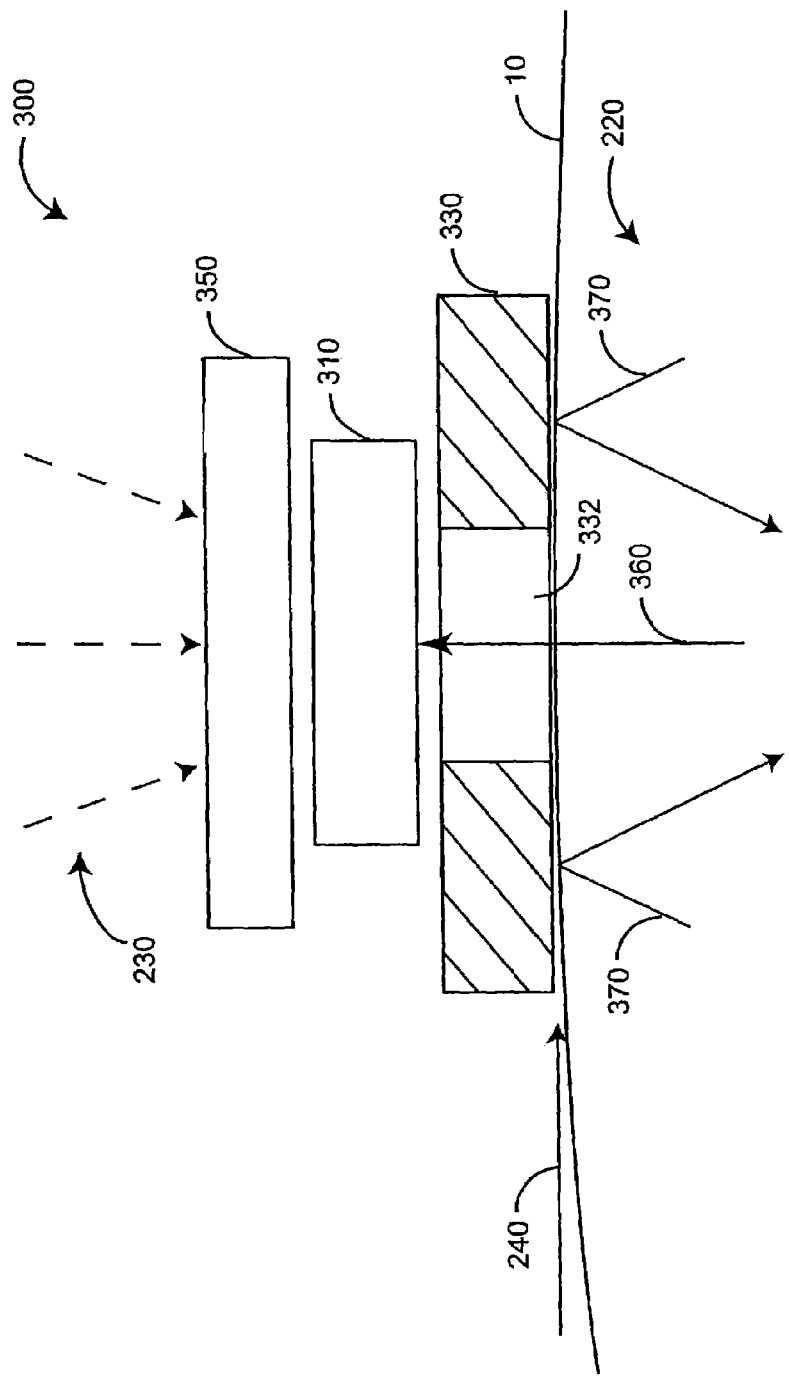
FIG. 3 is a diagram illustrating optical noise sources and a prior art reduced noise sensor.

FIGS. 4A–C illustrate a low noise optical housing 400 having a protruding cover 410, a generally flat flange 420 disposed around the periphery of the cover 410, and a generally flat base 460 adjoining the flange 420. The housing 400 is configured to accept a detector 820 (FIGS. 6A–B) and provide ambient light and piped light reduction. In particular, the low noise optical housing 400 advantageously incorporates the functions of a light barrier, opaque cover, spacer and aperture, as described with respect to FIG. 3, above, in a relatively small, easy to manufacture, one-piece design.

As shown in FIGS. 4B–C, the housing 400 is advantageously constructed of a flat substrate which, in one embodiment, is a laminate of two materials including an outer white layer 407 and an inner black layer 408. By utilizing a laminate of both white and black material, the low noise optical housing 400 advantageously functions both as a light absorber and as a light reflector. The white layer 407 acts as a reflector, reflecting unwanted ambient light outward from a detector enclosed in the housing, as described below, as well as reflecting emitter source light back into a patient tissue site. The reflected ambient light reduces noise and the reflected source light increases the sensor current transfer ratio. The black layer 408 absorbs unwanted ambient light, preventing it from reaching the enclosed detector 820 (FIGS. 6A–B). The two materials 407, 408 are laminated together before the housing 400 is formed and shaped. The housing 400 is vacuum formed on a flat blank of the laminated material to create a cover 410, as described below. The housing 400, aperture 470 and slot 480, as described below, are then punched out and the housing 400 is removed from the remainder of the laminated material.

In an alternative embodiment, the housing 400 is formed from a black substrate, which is painted white on the outside, i.e. the side corresponding to the outer white layer 407, or otherwise coated on the outside with a reflecting material or substance. In another alternative embodiment, the housing 400 is formed from a white substrate, which is painted black on the inside, i.e. the side corresponding to the inner black layer 408, or otherwise coated on the inside with an absorbing material or substance.

As shown in FIGS. 4A–C, the cover 410 has a ramp 412 sloping from the flange 420 to a generally level platform 414 raised above the flange 420. The cover 410 also has beveled sides 418 and a beveled back 419 that slope from the flange 420 inward to the platform 414. The cover 410 defines an pocket 440 for securing a detector 820 (FIGS. 6A–B), as described below. The flange 420 has indents 422 that gradually taper from the wider flange width 502 (FIG. 5A) to that of the narrower base width 503 (FIG. 5A).

Figure 12A:
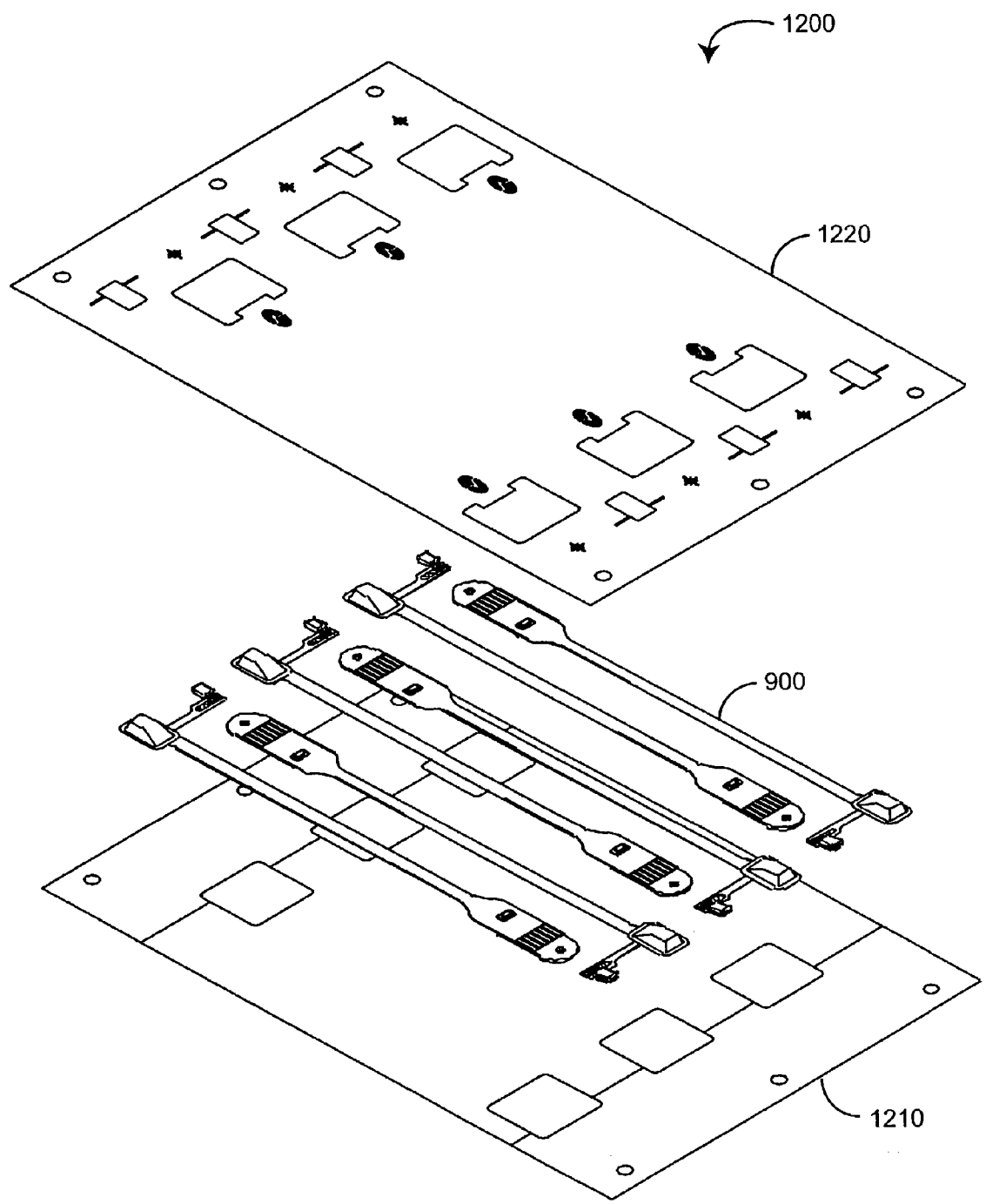
FIGS. 12A–B are exploded perspective views of multiple neonate sensor and adult sensor assemblies, respectively, showing base stock and face stock installation.
Figure 12B:
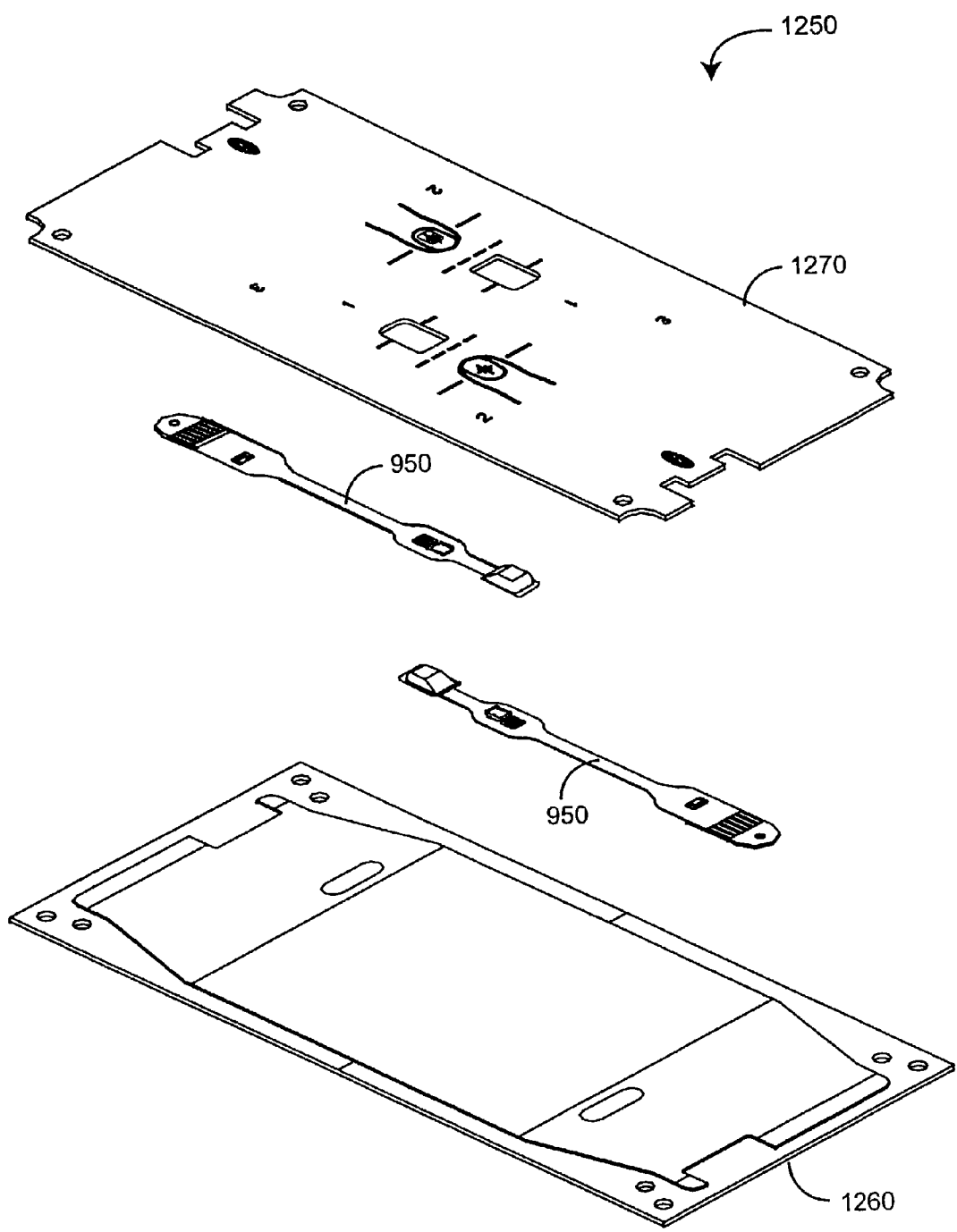

Also shown in FIGS. 4A–C, the base 460 defines a generally centered aperture 470 and a slot 480 proximate the flange 420, partially extending across the base width 503 (FIG. 5A). In a closed position, as described with respect to FIGS. 5C–D, below, the base 460 provides a bottom for the cover 410 and pocket 440 and optically shields the detector 820 (FIGS. 6A–B). The base 460 also provides a spacer and aperture to reduce light piping. The slot 480 allows the base 460 to be easily folded so that the aperture 470 is in proper alignment with the detector active area. Further, the narrower base width 503 (FIG. 5A) allows the flange 420 to overlap the base 460 in the closed position 560 (FIGS. 5C–D) so as to seal the housing edges from ambient light. The flange 420 also provides structure for attaching the housing 400 to a tape stock layer (FIGS. 12A–B).

FIGS. 5A–D illustrate the housing 400 in an open position 510 (FIGS. 5A–B) and a closed position 560 (FIGS. 5C–D). As shown in FIGS. 5A–B, in an open position 510 the housing 400 has an overall length 501, a flange width 502, a base width 503 and a thickness 504. The flange width 502 is greater than the base width 503. In one embodiment, the housing length 501 is less than about 1.1 inches, the flange width 502 is less than about 0.4 inches and the housing thickness 504 is less than about 0.015 inches. As shown in FIGS. 5A–D, from an open position 510, the housing 400 is folded to the closed position 560 along the slot 480 and across the base width 503 proximate to each indent 422. In the closed position 560, the housing 400 provides an optical enclosure for a detector, as described with respect to FIGS. 6A–B, below.

FIGS. 6A–B illustrate shielded detector assemblies 1000 incorporating flat aperture 400 and raised aperture 600 embodiments, respectively, of a low noise optical housing. A detector 820 is enclosed in the optical housing 400, 600 so that the active area of the photodiode chip 821 is aligned with the housing aperture 470, 670. An EMI shield 1010, described with respect to FIGS. 10A–C, below, also encloses the detector 820, and a corresponding flexible circuit assembly 801, described with respect to FIGS. 8–9, below, exits the housing 400, 600 between the base 460, 660 and the flange 420, 620. As shown in FIG. 6B, the raised aperture housing 600 includes a raised aperture portion 662 that extends from the plane of the base 660 so as to advantageously provide a larger spacing between the detector 820 and a tissue site, further reducing the effects of light piping.

FIGS. 7A–B illustrate an assembled pulse oximetry neonate sensor 700. The sensor 700 includes an optical end 701, an elongated body 703 and a connector end 705. The optical end 701 incorporates a detector assembly 1000 (FIGS. 10A–C), described below, including a low noise optical housing 400 (FIGS. 6A–B), as described above. The body 703 includes signal traces (not visible) between the optical end 701 and the connector end 705. The connector end 705 has a plug portion configured to insert into a mating patient cable connector so as to mechanically and electrically connect the sensor 700 to a patient cable 140 (FIG. 1), for example. A patient cable connector is described in U.S. Pat. No. 6,152,754 entitled "Circuit Board Based Cable Connector," which is assigned to Masimo Corporation, Irvine, Calif. and incorporated by reference herein.

Figure 7C:
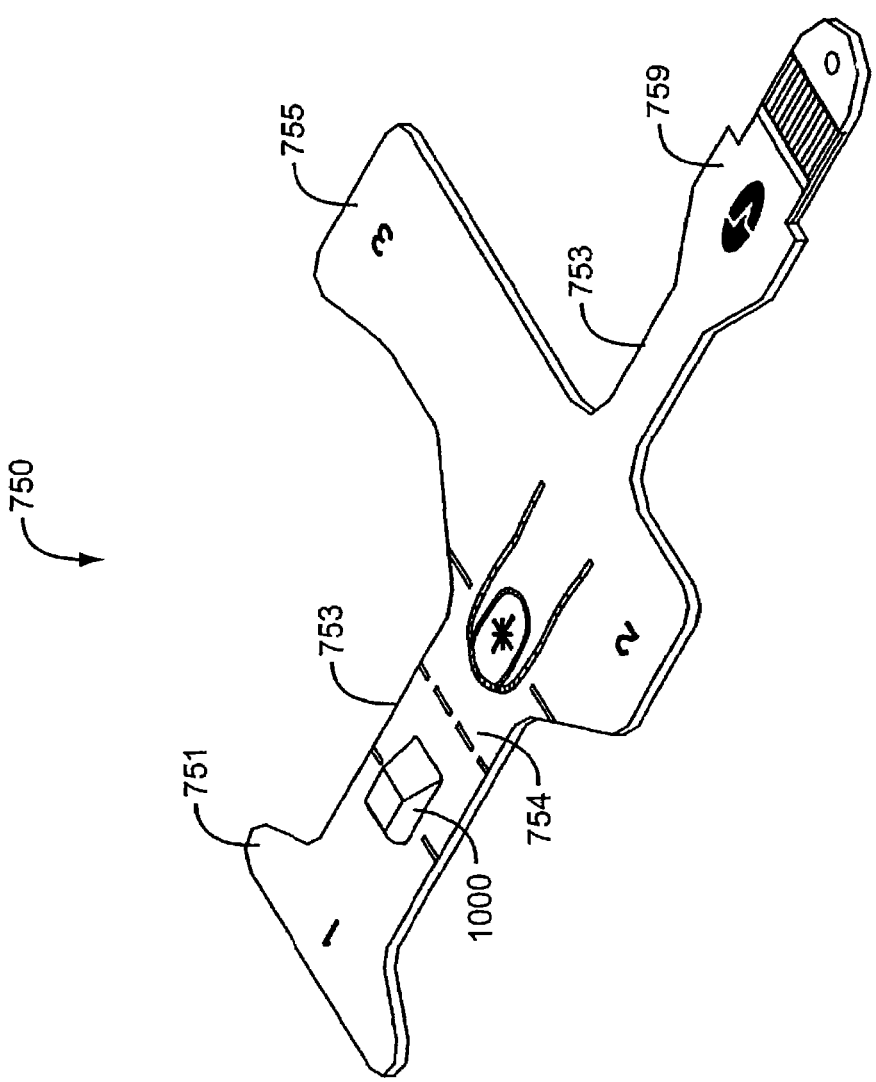
FIG. 7C is a perspective view of an assembled pulse oximetry sensor configured for an adult and incorporating a low noise optical housing.

FIG. 7C illustrates an assembled pulse oximetry adult sensor 750. The sensor 750 includes an end wrap 751, a body 753 including an optical section 754, a middle wrap 755, and a connector end 759. The optical section 754 incorporates a detector assembly 1000 similar in construction to that described in FIGS. 10A–C, below, including a low noise optical housing 400 (FIGS. 6A–B), as described above. The sensor 750 includes signal traces (not visible) between the optical section 754 and the connector end 759. The connector end 759 is similar to that described with respect to FIGS. 7A–B, above. A pulse oximetry adult sensor having end and middle wraps and an electromagnetic interference (EMI) shield is described in U.S. patent application Ser. No. 10/137,942, filed May 2, 2002, entitled "Flex Circuit Shielded Optical Sensor," assigned to Masimo Corporation, Irvine, Calif. and incorporated by reference herein.

Figure 1:
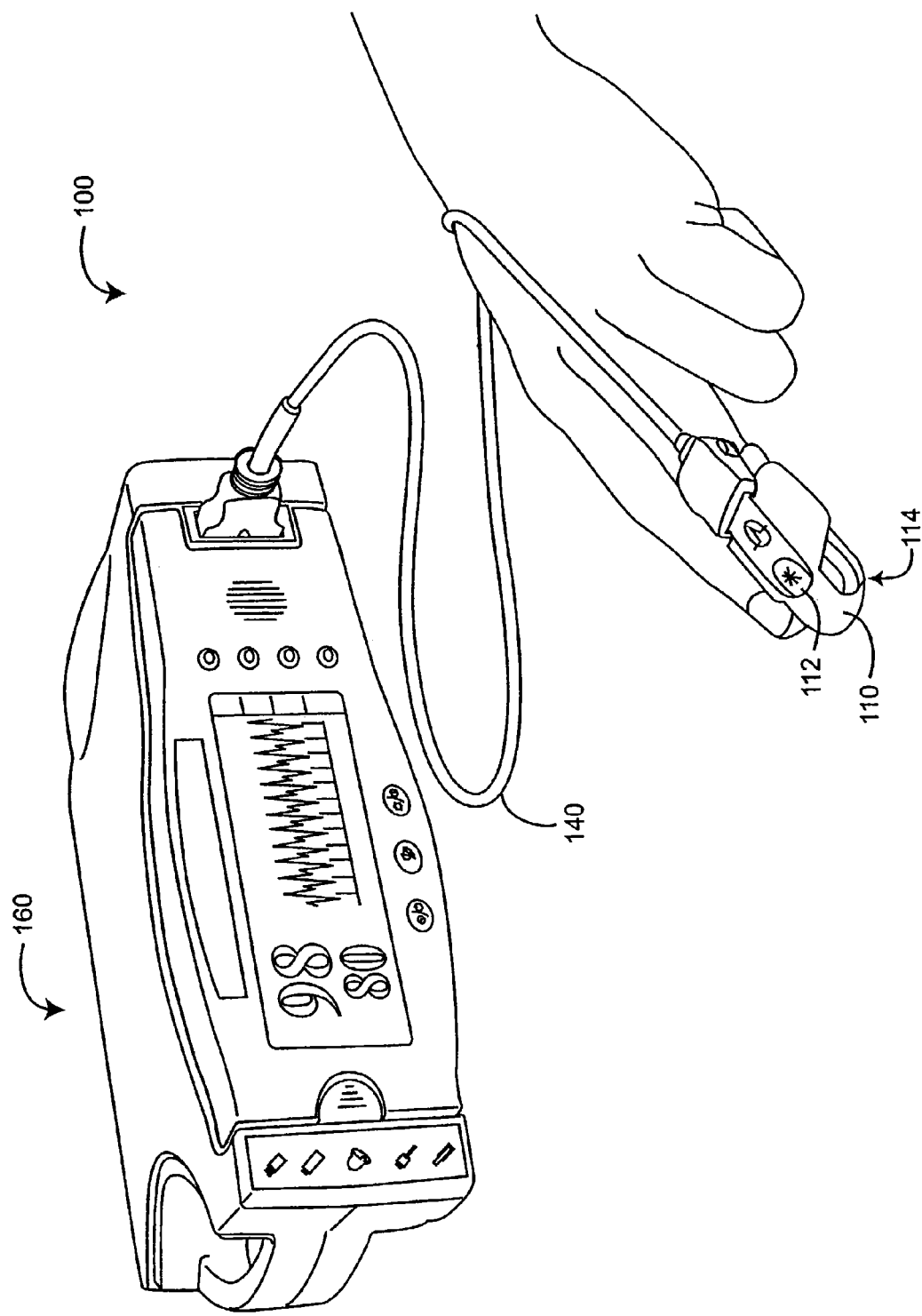
FIG. 1 is a perspective view of a prior art pulse oximetry system.
Figure 2:
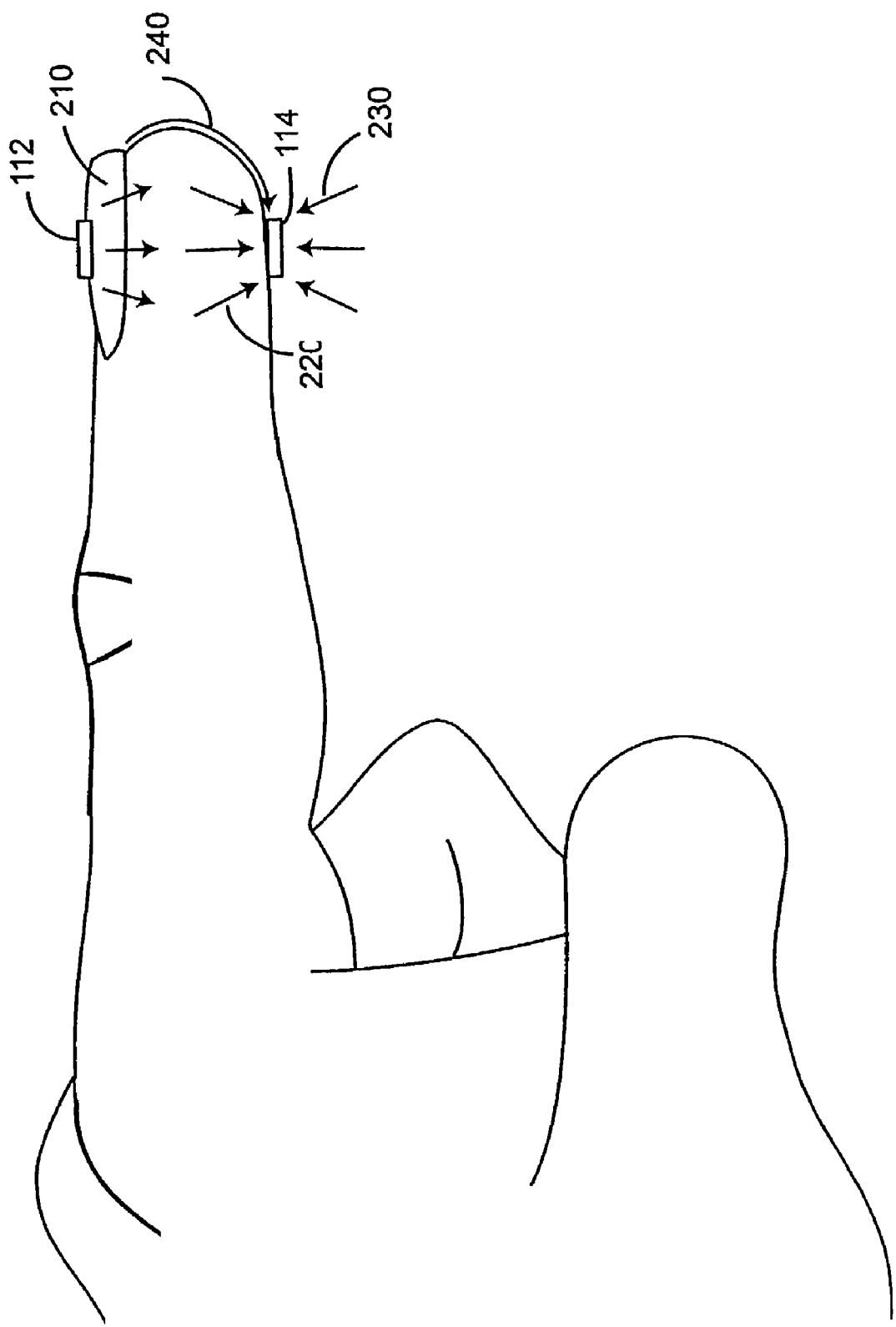
FIG. 2 is a diagram illustrating optical noise sources and a prior art sensor.

FIGS. 8–12 illustrate assembly of a neonate sensor 700 (FIGS. 7A–B) and an adult sensor 750 (FIG. 7C) including component attachment (FIGS. 8A–B), detector EMI shielding and optical shielding (FIGS. 9–11), and tape stock assembly (FIGS. 12A–B). FIG. 8A illustrates a neonate sensor circuit assembly 800 including multiple, duplicate flexible circuit assemblies 801 each having a flexible circuit substrate 810 and associated components soldered or otherwise electrically connected to the flexible circuit substrate 810, as is well known in the art. Each flexible circuit assembly 801 includes a detector 820 and an emitter 830. The detector 820 is enclosed in an EMI shield 1010, described in further detail with respect to FIGS. 10A–C, below. The emitter 830 is connected to a pad 1110 having multiple contact sets, described in further detail with respect to FIG. 11A, below. Each assembly 801 may also include an information element 840, which can be read by an attached pulse oximeter 160 (FIG. 1). The information element 840 may provide information regarding the sensor 700, such as sensor type or manufacturer to name a few. An information element is described in U.S. Pat. No. 6,397,091, entitled "Manual and Automatic Probe Calibration," assigned to Masimo Corporation, Irvine, Calif. and incorporated by reference herein.

Figure 8A:
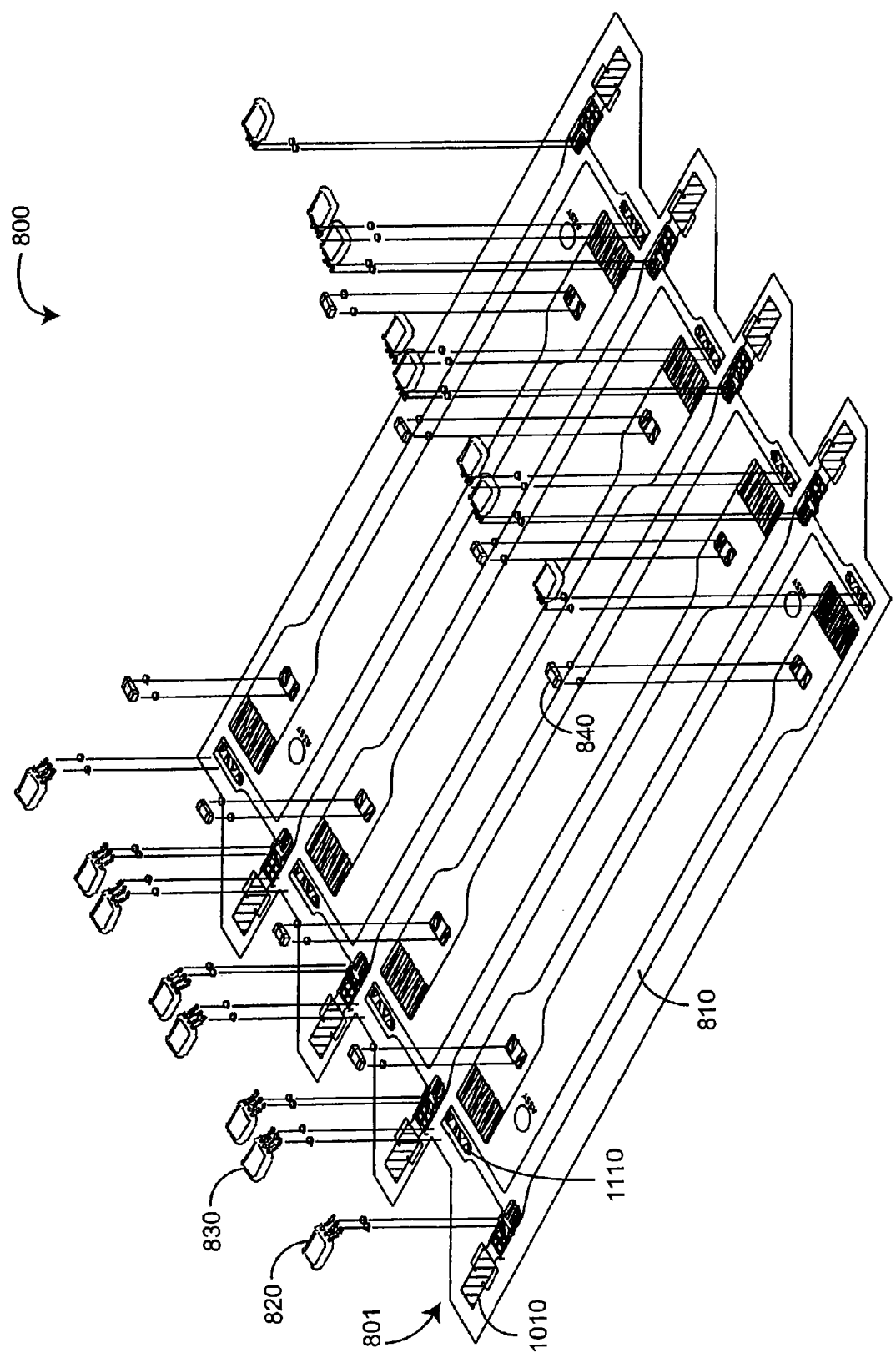
FIGS. 8A–B are exploded perspective views of neonate and adult flexible circuit assemblies, respectively, configured for a low noise optical housing.
Figure 8B:
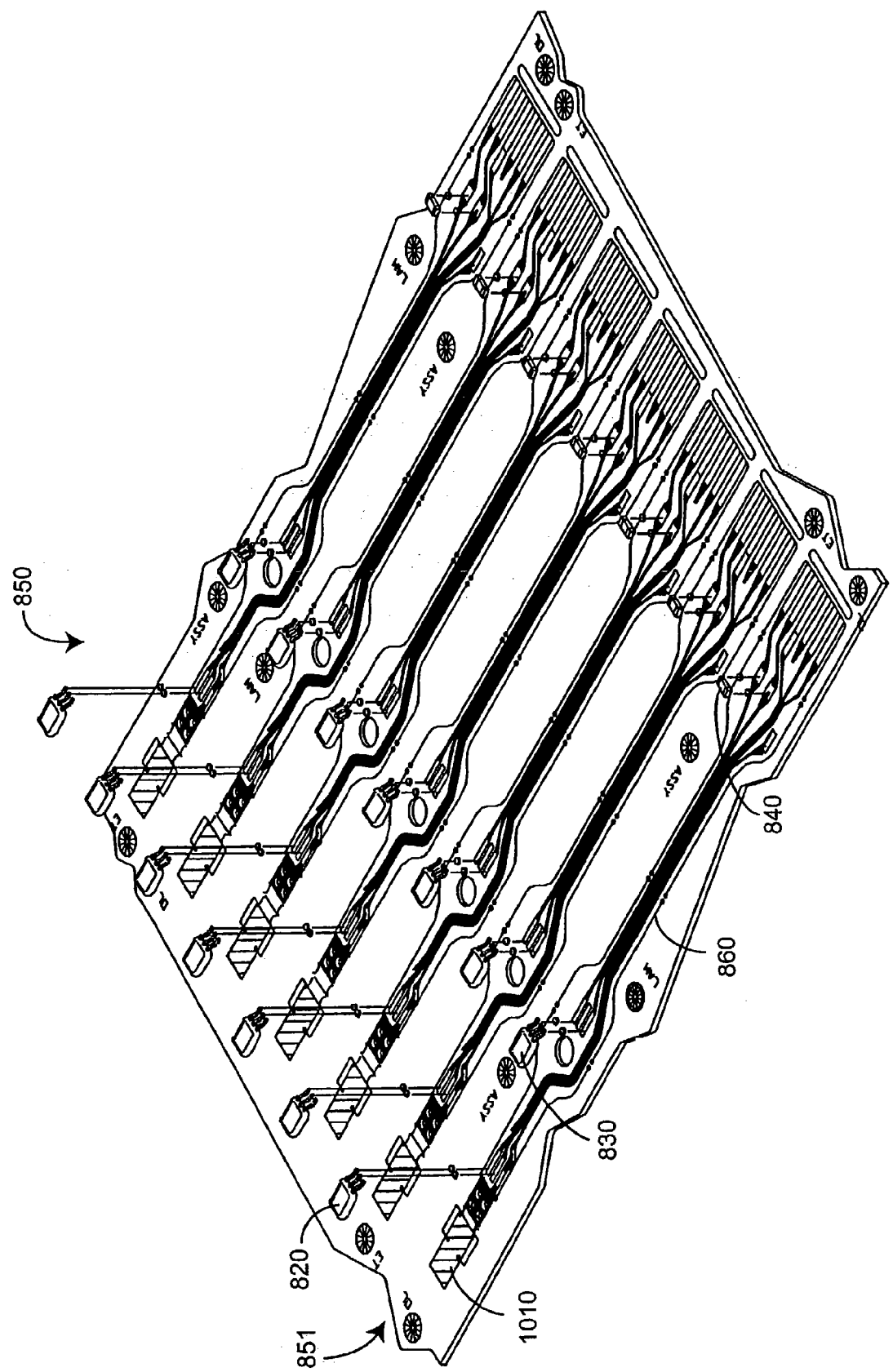

FIG. 8B illustrates an adult sensor circuit assembly 850 likewise including multiple, duplicate flexible circuit assemblies 851 each having a flexible circuit substrate 860 and associated components soldered or otherwise electrically connected to the flexible circuit substrate 860, including a detector 820, an emitter 830 and maybe an information element 840, such as described with respect to FIG. 8A, above. The detector 820 is enclosed in an EMI shield 1010, such as described with respect to FIGS. 10A–C, below. In one embodiment, the emitter 830 is connected to a pad 1160 (FIGS. 11C–E) having extended contacts, as described below.

FIGS. 9A–B illustrate a neonate sensor assembly 900 having a flexible circuit assembly 801, a low noise optical housing 400 and a connector tab 910. The sensor assembly 900 is configured as an optical portion 1100, which is described in further detail with respect to FIGS. 11A–B, below, and a connector portion 901. The optical portion 1100 has an emitter 830 and a shielded detector assembly 1000, described in further detail with respect to FIGS. 10A–C. The connector portion 901 is configured with the connector tab 910 supporting sensor pinouts 920.

FIGS. 9C–D illustrate an adult sensor assembly 950 having a flexible circuit assembly 851, a low noise optical housing 400 and a connector tab 910. The sensor assembly 950 is configured as an optical portion 1150, described in further detail with respect to FIGS. 11C–E, below, and a connector portion 901, as described above. The optical portion 1150 has an emitter 830 and a shielded detector assembly 1000, such as is described in detail with respect to FIGS. 10A–C.

Figure 10B:
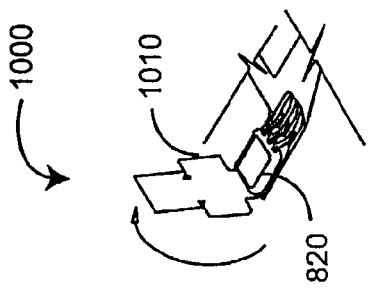
FIGS. 10A–C are detailed perspective views of an unassembled, a partially assembled and a fully assembled EMI shield, respectively, prior to low noise optical housing installation.
Figure 10A:
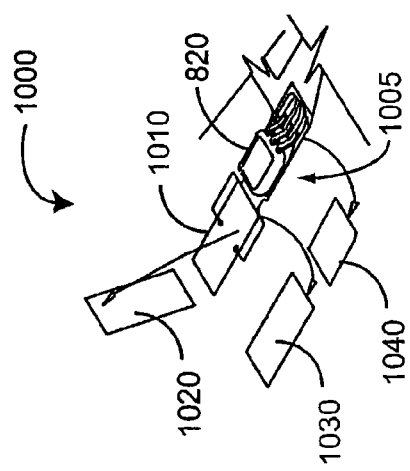
Figure 10C:
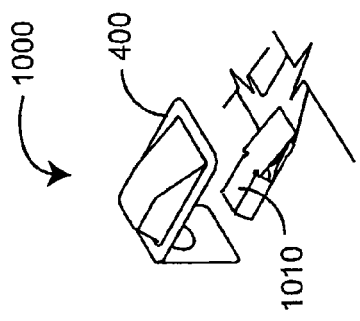

FIGS. 10A–C illustrate a shielded detector assembly 1000 configured for the neonate flexible circuit assembly 801 (FIGS. 8A, 9A–B) as shown, or, similarly, for the adult flexible circuit assembly 851 (FIGS. 8B, 9C–D). As shown in FIG. 10A, inside pressure sensitive adhesive (PSA) 1020 and top PSA 1030 are removed from a foldable shield 1010, and bottom PSA 1040 is removed from a fixed shield 1005 (not visible). As shown in FIG. 10B, the shield 1010 is next folded toward the detector 820. As shown in FIG. 10C, the shield 1010 is then folded over the back and sides of the detector 820, enclosing the detector 820. The inside PSA 1020 adheres to the detector 820, maintaining the foldable shield 1010 in place. Next, the EMI shielded detector 820 is placed into the optical housing 400. The top PSA 1030 adheres to the inside surface of the optical housing 400, which defines a pocket 440 (FIGS. 4B–C) as described above. The bottom PSA 1040 adheres to the optical housing base 410 (FIGS. 4A–C), maintaining the detector 820 in place within the optical housing cover 410 (FIGS. 4A–C), aligned with the aperture 470 (FIG. 4A), and maintaining the optical housing 400 in the closed position 560 (FIGS. 5C–D).

Figure 11B:
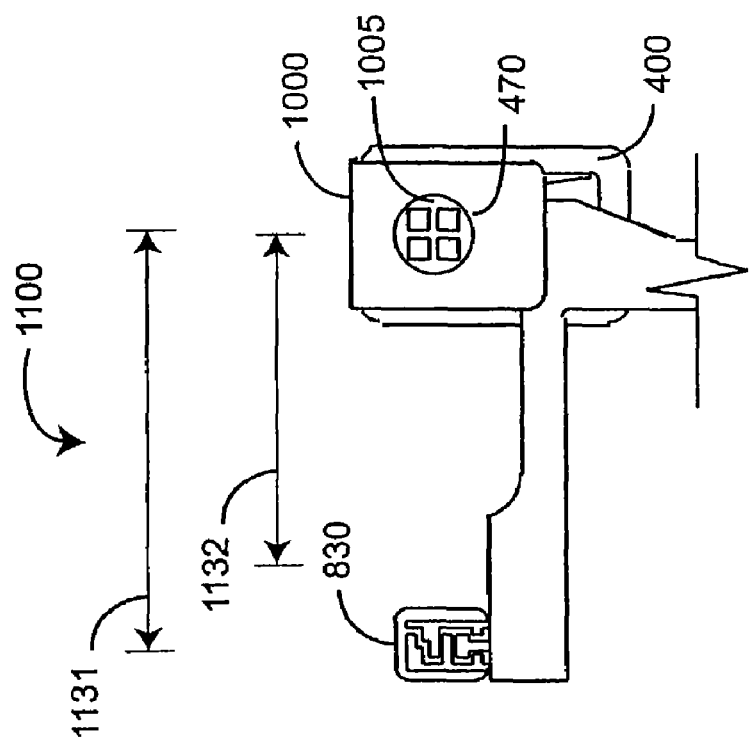
FIGS. 11A–B are detailed top and bottom views of a neonate or infant sensor optical assembly.
Figure 11A:
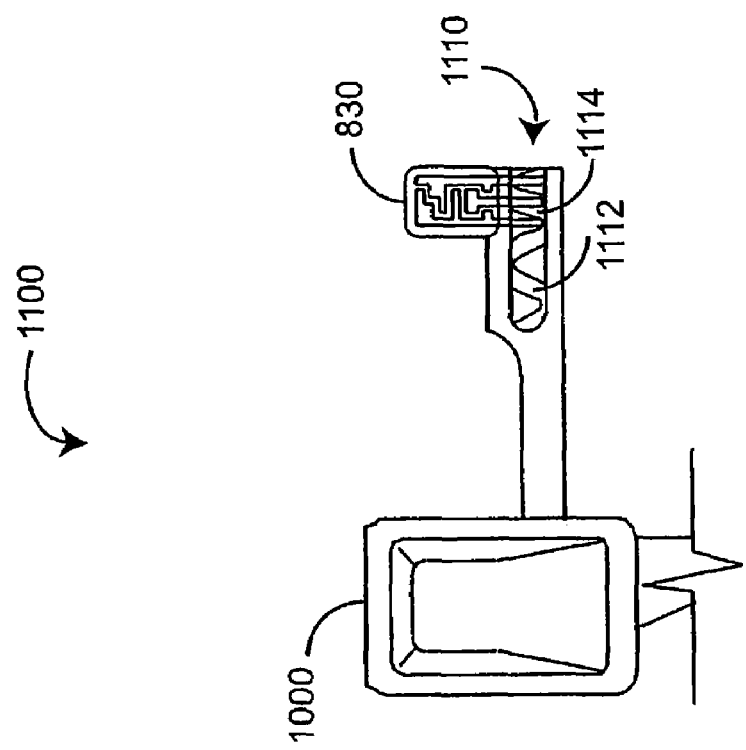

FIGS. 11A–B illustrate one embodiment of the optical portion 1100 of a sensor assembly 900 (FIGS. 9A–B) having a detector assembly 1000 and an emitter 830 connected to a pad 1110. As shown in FIG. 11A, a particular embodiment of the pad 1110 advantageously has an inner contact set 1112 and an outer contact set 1114. The emitter 830 may be attached and electrically connected in a first position to the inner contact set 1112 or in a second position to the outer contact set 1114. As shown in FIG. 11B, this advantageously provides two different detector-emitter spacings 1131, 1132 on the same flexible circuit substrate. A comparatively wider spacing 1131 corresponds to the second emitter position attached to the outer contact set 1114 (shown), and a comparatively narrower spacing 1132 corresponds to the first emitter position attached to the inner contact set 1112 (not shown). The choice of mounting the emitter with a narrower or wider spacing accommodates different sensor types for different sized patients or different tissue site thicknesses with fewer unique sensor parts or subassemblies. Note that the detector 820 (FIGS. 10A–B) is not visible in FIG. 11B as it is behind the fixed shield 1005. As an example, a neonate sensor 700 (FIGS. 7A–B) and an infant sensor (not illustrated) configured for different sized foot sites may be manufactured from a single flex circuit part. In a preferred embodiment, the inner pads are configured for a 20 mm detector-emitter spacing appropriate for a neonate, such as a child weighing under 3 kg and the outer pads 1114 are configured for a 25 mm detector-emitter spacing appropriate for an infant, such as a child weighing 3–10 kg.

In another embodiment of the optical portion 1100, a reinforcing tape (not shown) is applied to the component side (shown in FIG. 11A) of the flexible circuit between the detector assembly 1000 and the emitter 830 so as to increase the number of bend cycles before failure of that flexible circuit area and to improve electrostatic discharge (ESD) resistance. The reinforcing tape is disposed over at least the extent of the pad 1110. In a particular embodiment, the reinforcing tape is 0.004 inch polypropylene.

Figures 11C, 11D, 11E:
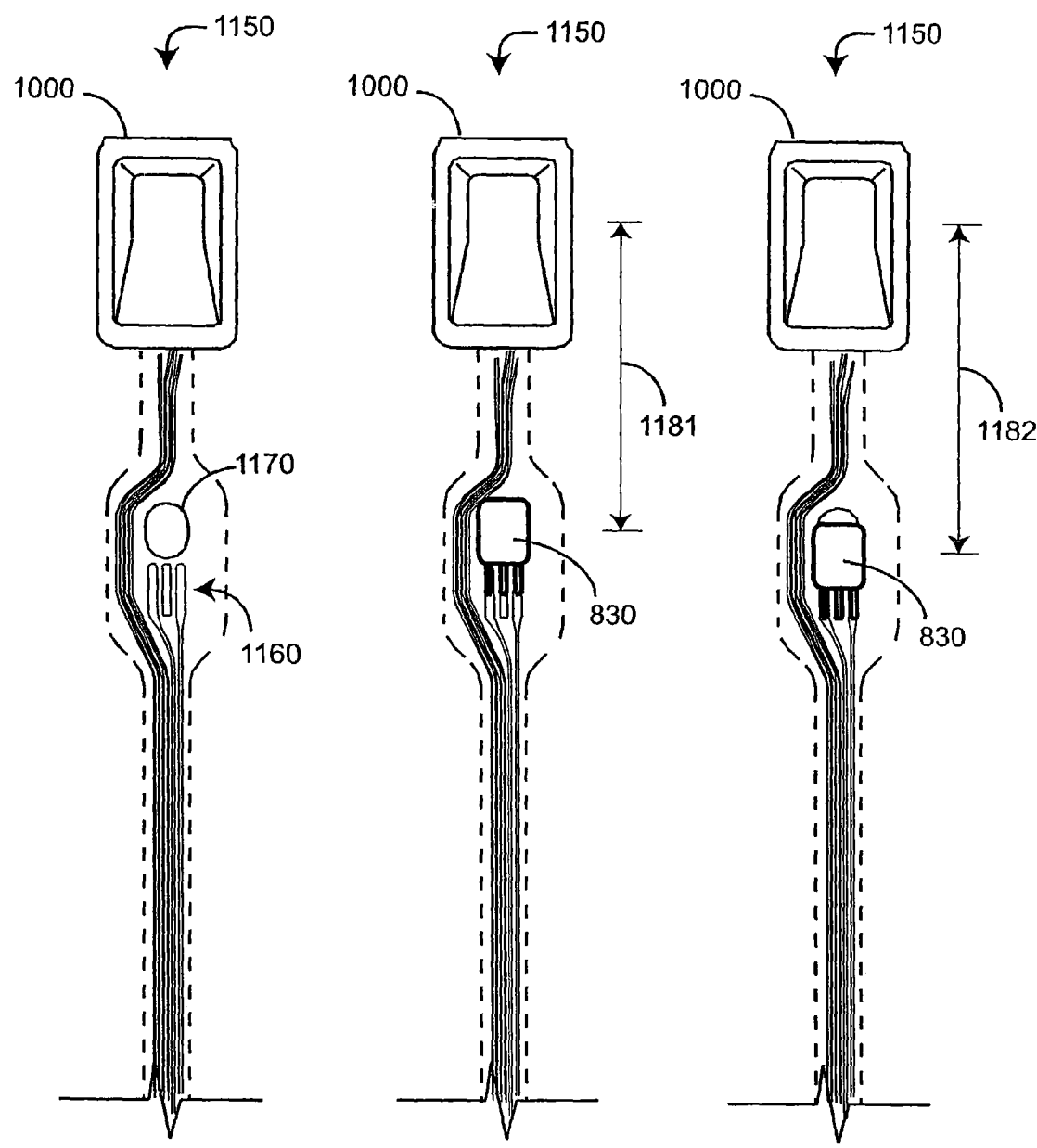
FIGS. 11C–E are detailed top views of an adult or pediatric sensor optical assembly.

FIGS. 11C–E illustrate one embodiment of the optical portion 1150 of a sensor assembly 950.(FIGS. 9C–D) having a detector assembly 1000 and an emitter 830 connected to a pad 1160 having extended contacts. The contacts are extended along the direction between the detector assembly 1000 and the emitter 830, allowing the emitter to be mounted on the same pad 1160 in multiple positions. As shown in FIG. 11C, the emitter 830 is installed over an elongated aperture 1170. The extended pad area 1160 advantageously provides for different detector-emitter spacings 1181, 1182 (FIGS. 11D–E) on the same flexible circuit substrate. A comparatively narrower spacing 1181 corresponds to a first emitter position (FIG. 11D), and a comparatively wider spacing 1182 corresponds to a second emitter position (FIG. 11E). This accommodates different sensor types for different sized patients or different tissue site thicknesses with fewer unique sensor parts or subassemblies. As an example, an adult sensor 750 (FIGS. 7C) and a pediatric sensor (not shown) configured for different sized finger sites may be manufactured from a single flex circuit part. As shown in FIGS. 11D–E, in a preferred embodiment, the pad 1160 (FIG. 11C) is configured with contacts that are extended at least 0.1 inches beyond an emitter 830 nominal lead length so as to accommodate a 1.0 inch detector-emitter spacing 1181 appropriate for a pediatric sensor or a 1.1 inch detector-emitter spacing 1182 appropriate for an adult sensor. The elongated aperture 1170 (FIG. 11C) is configured accordingly, i.e. is elongated from a circular aperture sufficiently to accommodate either a 1.0 inch or a 1.1 inch detector-emitter spacing.

The ability to adjust the detector-emitter spacing on a particular flexible circuit so as to minimize the number of unique parts in manufacturing various sensor types and sizes is disclosed above. That disclosure is with respect to a pad 1110 (FIG. 11A) having multiple contact sets and a pad 1160 (FIG. 11C) having extended contacts with an associated elongated aperture 1170 (FIG. 11C). One of ordinary skill in the art will recognize other electrical and mechanical structures that allow such detector-emitter spacing adjustment. For example, although adjustment of the emitter 830 location relative to the detector 820 is achieved by the above-disclosed embodiments, adjustment of the detector 820 location relative to the emitter 830 may be achieved with similar structures. Further, adjustment of the detector-emitter spacing may also be achieved by altering the orientation of the detector 820 and/or the emitter 830. These adjustments may also be accommodated by multiple apertures rather than an elongated aperture. Although the sensors disclosed are based upon the detection of light transmitted through a tissue site, the ability to adjust detector-emitter spacing is equally applicable to reflectance sensors, i.e. sensors that are based upon the detection of light reflected from a tissue site.

FIG. 12A illustrates a tape stock assembly 1200 for a neonate sensor. In particular, multiple sensor assemblies 900 are sandwiched between a base stock 1210 and a face stock 1220. Individual completed sensors 700 (FIGS. 7A–B) are then cut from the tape stock assembly 1200. A base stock and a face stock are described in U.S. Pat. No. 5,782,757, cited above.

FIG. 12B illustrates a tape stock assembly 1250 for an adult sensor. In particular, multiple sensor assemblies 950 are sandwiched between a base stock 1210 and a face stock 1220. Individual completed sensors 750 (FIGS. 7C) are then cut from the tape stock assembly 1250.

The low noise optical housing has been disclosed in detail in connection with various embodiments. These embodiments are disclosed by way of examples only and are not to limit the scope of the claims that follow. One of ordinary skill in the art will appreciate many variations and modifications.

Additionally, all publications, patents, and patent applications mentioned in this specification are herein incorporated by reference to the same extent as if each individual publication, patent, or patent application was specifically and individually indicated to be incorporated by reference.

What is claimed is:

1. A sensor circuit comprising:
   a circuit substrate;
   a pair of pads disposed on an optical portion of said circuit substrate;
   a plurality of pinouts disposed on a connector portion of said circuit substrate; and a plurality of conductive paths providing electrical communication between said pads and said pinouts, said pads configured to mechanically mount a corresponding pair of optical components to said circuit substrate and to electrically connect said components to said conductive paths, at least one of said pads adapted to mount one of said components at either a first spacing or a second spacing from the other one of said components, said first and second spacings corresponding to particular sensor types, and said second spacing being greater than said first spacing by a predetermined amount.

2. The sensor circuit according to claim 1 wherein said at least one of said pads comprises a plurality of extended contacts providing a first attachment position corresponding to said first spacing and a second attachment position corresponding to said second spacing.

3. The sensor circuit according to claim 1 wherein said at least one of said pads comprises a first contact set of contacts corresponding to said first spacing and a second contact set corresponding to said second spacing, said first contact set and said second contact set being electrically connected in parallel.

4. The sensor circuit according to claim 1 further comprising an elongated aperture defined by said substrate and adapted to transmit light through said substrate for said one of said components mounted at either said first spacing or said second spacing.

5. The sensor circuit according to claim 1 wherein said first spacing is about 20 mm and said second spacing is about 25 mm.

6. The sensor circuit according to claim 1 wherein said first spacing is about 1.0 inch and said second spacing is about 1.1 inch.

7. A sensor circuit comprising:
a flexible circuit substrate;
a first pad disposed on said substrate and configured to mount a detector; and
a second pad disposed on said substrate and configured to mount an emitter,
at least one of said first pad and said second pad adapted so that a detector-emitter spacing is a first distance or a second distance depending on the placement of at least one of said detector and said emitter,
said first distance and said second distance predetermined and corresponding to particular sensor types.

8. The sensor circuit according to claim 7 wherein:
said second pad comprises a first contact set and a second contact set,
said emitter mountable to said first contact set said first distance from said detector mounted to said first pad, and
said emitter mountable to said second contact set said second distance from said detector mounted to said first pad.

9. The sensor circuit according to claim 7 wherein:
said second pad comprises a plurality of extended contacts,
said emitter mountable to said contacts in a first position located a first distance from said detector mounted to said first pad, and
said emitter mountable to said contacts in a second position located a second distance from said detector mounted to said first pad.

10. The sensor circuit according to claim 9 further comprising an elongated aperture configured so that light is transmitted from said emitter through said aperture when said emitter is mounted in either said first position or said second position.

11. The sensor circuit according to claim 7 wherein said sensor types comprise a neonate sensor and an infant sensor, said first distance and said second distance in the range of about 20 mm to about 25 mm.

12. The sensor circuit according to claim 7 wherein said sensor types comprise a pediatric sensor and an adult sensor, said first distance and said second distance in the range of about 1.0 in. to about 1.1 in.

13. A sensor circuit method comprising the steps of:
predetermining a plurality of optical component spacings based upon a corresponding plurality of sensor types, said sensor types indicative of tissue site location and patient size;
configuring a pad to fixedly mount and electrically connect an optical component to a flexible circuit at a plurality of positions, said positions corresponding to said spacings; and
mounting said optical component to a particular one of said positions to construct a particular one of said sensor types.

14. The sensor circuit method according to claim 13 comprising the further step of adapting at least one aperture defined by said flexible circuit so as to pass light for said optical component mounted at any of said positions.

15. The sensor circuit method according to claim 13 wherein said configuring step comprises the substep of constructing a plurality of contact sets electrically connected in parallel, each of said sets providing a corresponding one of said positions.

16. The sensor circuit method according to claim 13 wherein said configuring step comprises the substep of providing a plurality of contacts extending from said optical component so that said optical component is mountable to said contacts in each of said positions.

* * * * *

UNITED STATES PATENT AND TRADEMARK OFFICE
CERTIFICATE OF CORRECTION

PATENT NO. : 7,096,054 B2 Page 1 of 1
APPLICATION NO. : 10/632012
DATED : August 22, 2006
INVENTOR(S) : Abdul-Hafiz et al.

It is certified that error appears in the above-identified patent and that said Letters Patent is hereby corrected as shown below:

Sheet 16 of 17, Fig. 12A, below "Figure" delete "FIG 12A" and insert -- FIG. 12A --, therefore.

At column 2, line 25, delete "a the" and insert -- a detector within the --, therefore.

At column 2, line 49, delete "mount." and insert -- amount. --, therefore.

At column 2, line 50, delete "comprisesa" and insert -- comprises a --, therefore.

At column 3, line 35 (Approx.), after "top" delete "arid" and insert -- and --, therefore.

At column 4, line 2, after "spacing;" delete "and".

At column 4, line 56, after "defines" delete "an" and insert -- a --, therefore.

At column 7, line 53, delete "950.(FIGS." and insert --.950 (FIGS. --, therefore.

At column 8, line 2, after "750" delete "(FIGS." and insert -- (FIG. --, therefore.

At column 8, line 48, after "750" delete "(FIGS." and insert -- (FIG. --, therefore.

Signed and Sealed this

Nineteenth Day of June, 2007

JON W. DUDAS
*Director of the United States Patent and Trademark Office*